(12) United States Patent
Kino et al.

(10) Patent No.: US 7,130,042 B2
(45) Date of Patent: Oct. 31, 2006

(54) DUAL AXIS FLUORESCENCE MICROSCOPE WITH MODULATED INPUT

(75) Inventors: Gordon S. Kino, Stanford, CA (US); Michael J. Mandella, Cupertino, CA (US)

(73) Assignee: Board of Trustees of the Leland Stanford Junior University, Stanford, CA (US)

( * ) Notice: Subject to any disclaimer, the term of this patent is extended or adjusted under 35 U.S.C. 154(b) by 412 days.

(21) Appl. No.: 10/794,561

(22) Filed: Mar. 5, 2004

(65) Prior Publication Data

US 2004/0173760 A1  Sep. 9, 2004

Related U.S. Application Data

(60) Provisional application No. 60/452,838, filed on Mar. 6, 2003.

(51) Int. Cl.
  *G01J 3/30* (2006.01)
  *G01J 1/58* (2006.01)

(52) U.S. Cl. .................................. 356/318; 250/458.1

(58) Field of Classification Search ................ 356/317, 356/318, 417; 359/368–398; 250/458.1, 250/459.1, 461.1, 461.2; 422/82.07, 82.08; 436/172
  See application file for complete search history.

(56) References Cited

U.S. PATENT DOCUMENTS

| | | | |
|---|---|---|---|
| 5,018,866 A * | 5/1991 | Osten .......................... | 356/417 |
| 5,034,613 A | 7/1991 | Denk et al. ............... | 250/458.1 |
| 5,162,648 A | 11/1992 | Iwasaki ...................... | 250/216 |
| 5,973,828 A | 10/1999 | Webb .......................... | 359/385 |
| 6,294,327 B1 * | 9/2001 | Walton et al. ............... | 359/368 |
| 6,351,325 B1 | 2/2002 | Mandella et al. ........... | 359/210 |
| 6,369,928 B1 * | 4/2002 | Mandella et al. ........... | 359/385 |
| 6,381,023 B1 | 4/2002 | Kempe ........................ | 356/484 |
| 6,423,956 B1 * | 7/2002 | Mandella et al. ........... | 359/385 |
| 6,441,356 B1 | 8/2002 | Mandella et al. ........ | 250/201.3 |
| 6,642,504 B1 | 11/2003 | Cathey, Jr. ................... | 250/216 |
| 2005/0046848 A1 * | 3/2005 | Cromwell et al. .......... | 356/417 |
| 2005/0046849 A1 * | 3/2005 | Cromwell et al. .......... | 356/417 |

* cited by examiner

*Primary Examiner*—Gregory J. Toatley, Jr.
*Assistant Examiner*—Patrick Connolly

(57) ABSTRACT

A dual beam confocal microscope is provided. An optical source assembly provides two mutually coherent optical beams differing in frequency by a frequency difference $\Delta f$. The two beams are received by focusing assemblies that provide two focused beams to a sample. The focused beams intersect at a beam intersection angle within a target region of the sample. The two focused beams have respective focal regions preferably overlapping with the target region. A detector receives radiation emitted from the sample, including radiation emitted from the target region. The detector output, responsive to received intensity, is filtered with an electrical filter to provide a filtered signal. The electrical filter has a frequency response $H(f)$, where $H(f)$ has a pass band including $f=\Delta f$ and a stop band including $f=0$. Optionally, an optical filter and/or a collection assembly can be placed between the sample and detector.

40 Claims, 5 Drawing Sheets

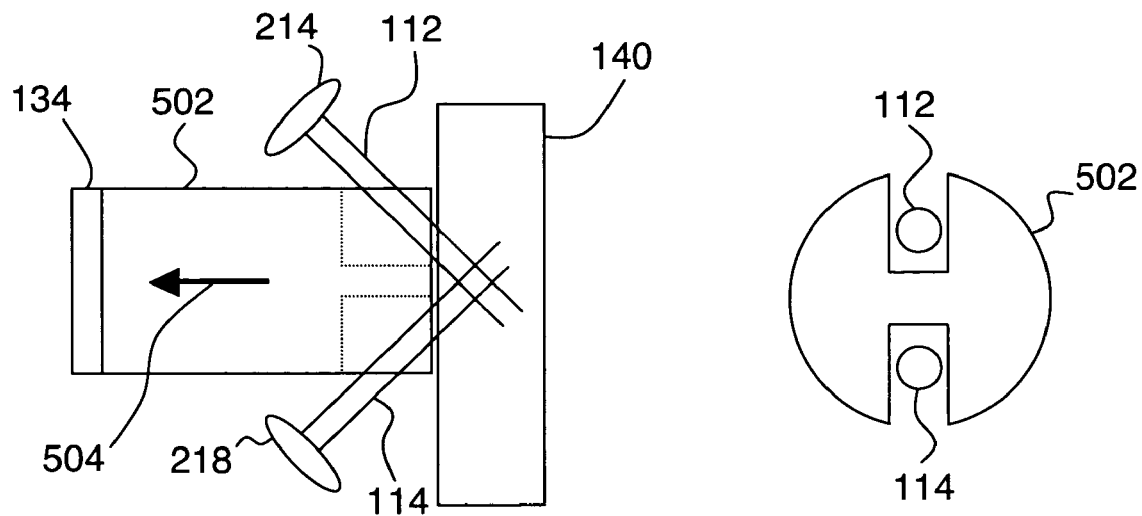
Fig. 5a
Fig. 5b
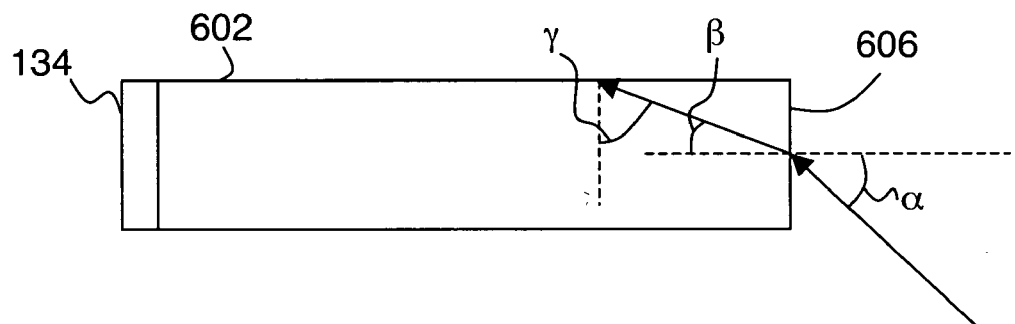
Fig. 6a
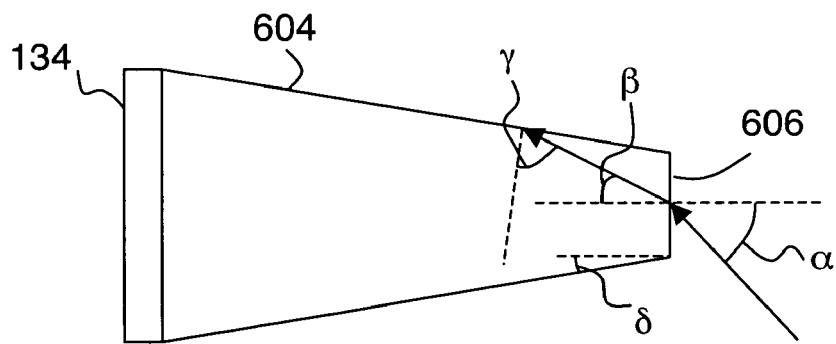
Fig. 6b

DUAL AXIS FLUORESCENCE MICROSCOPE WITH MODULATED INPUT

CROSS REFERENCE TO RELATED APPLICATIONS

This application is related to, and claims priority from, U.S. provisional application No. 60/452,838 filed on Mar. 6, 2003 and hereby incorporated by reference.

FIELD OF THE INVENTION

This invention is related to confocal microscopy.

BACKGROUND

Conventional wide field microscopy is based on formation of a high-magnification image of an illuminated sample using conventional microscope optics. In contrast, confocal microscopy is based upon the selective illumination of a small part of the sample, referred to as a target region, and on the selective collection of light emitted from the target region. Image formation is accomplished by scanning the position of the target region within the sample. Typically, the sample is illuminated with an illumination beam which is brought to a diffraction-limited (or nearly so) focus within the sample. Light emitted by the part of the sample within the focal region of the illumination beam is selectively collected and detected.

It is helpful to define an observation beam as being the beam that would be present if the optical detector in the above selective collection and detection arrangement were replaced by an optical source. Parts of the sample outside the observation beam are generally "not seen" by the detector. Thus the overlap of the illumination beam and observation beam defines the target region. Since it is generally desirable to decrease the size of the target region as much as possible, the illumination beam and observation beam are typically both brought to a small diffraction-limited focus (e.g., using a high numerical aperture (NA) lens having low aberration). Furthermore, the focal regions of the illumination beam and observation beam typically overlap (i.e., the two beams are typically confocal).

In the earliest confocal microscopes, the illumination beam and observation beams are collinear. In fact, frequently the same optical elements define the observation and illumination beams, and the observed signal is separated from the illumination light with a beamsplitter or directional coupler. When a beam is brought to a focus, the resulting focal region typically has an axial dimension several times larger than its transverse dimensions, especially if the focusing numerical aperture is less than 0.5. Here the axial direction is along the beam axis and the transverse directions are perpendicular to the beam axis. Thus, collinear illumination and observation beams typically provide a generally "cigar shaped" target region, having an axial dimension several times larger than its transverse dimensions.

More recently, for example in U.S. Pat. No. 5,973,828, non-collinear illumination and observation beams have been employed. Since the two beams intersect at an angle, the resulting target region is smaller than it would be for collinear beams. In particular, the target region can be roughly spherical and can have a radius on the order of the transverse beam dimensions.

A further variation on non-collinear illumination and observation beams is considered in U.S. Pat. No. 6,369,928, where two non-collinear illumination beams are supplied to the sample. In this arrangement, the illumination beam optics can conveniently define non-collinear observation beams (e.g., illumination optics 1 defines observation beam 2 and vice versa). Alternatively, light emitted from a sample region where the two illumination beams overlap can be selectively collected by optics other than the illumination beam optics.

However, the selective collection of light from such an arrangement poses a number of practical difficulties, especially when fluorescence radiation is of interest. For example, it is generally desirable to collect as much light as possible, and light collection increases as the lens NA increases because light from the sample is usually emitted in all directions. But, aberration of a simple lens also increases as lens NA increases, which usually obliges a lens designer to make a critical trade between resolution, complexity, working distance, and light collection efficiency. Thus high resolution microscope objectives can provide high NA, but the resulting designs are complex and bulky, and tend to provide a short working distance. This trade is applicable to both fluorescence microscopy and reflection/scattering microscopy. Furthermore, fluorescence is often emitted over a broad range of wavelengths, thus fluorescence confocal microscopes usually must further include chromatic aberration in the above trade, which greatly complicates their design. Finally, some applications, such as in vivo imaging require long working distances which are difficult to provide with high NA lenses.

Accordingly, it would be an advance in the art to provide a dual-illumination beam confocal microscope having a less critical trade between light collection, chromatic aberration, complexity, working distance, and resolution.

SUMMARY

The present invention provides a dual beam confocal microscope. An optical source assembly provides two mutually coherent optical beams differing in frequency by a frequency difference $\Delta f$. The two beams are received by focusing assemblies that provide two focused beams to a sample. The focused beams intersect at a beam intersection angle within a target region of the sample. The two focused beams have respective focal regions preferably overlapping with the target region. A detector receives radiation emitted from the sample, including radiation emitted from the target region. The detector output, responsive to received intensity, is filtered with an electrical filter to provide a filtered signal. The electrical filter has a frequency response $H(f)$, where $H(f)$ has a pass band including $f=\Delta f$ and a stop band including $f=0$. Optionally, an optical filter (to block scattered and/or reflected light but pass fluorescence) and/or a collection assembly can be placed between the sample and detector.

Within the target region of the sample, the incident optical intensity periodically varies with frequency $\Delta f$, due to interference between the two focused mutually coherent beams. Within parts of the sample illuminated by only one of the two focused beams, there is no periodic intensity modulation of the incident optical intensity. Similarly, light originating from the target region will be periodically modulated, and light originating from outside the target region will not be modulated. The combination of detector and filter passes the part of the signal from the modulated light and blocks the part of the signal from un-modulated light. The filter output signal is responsive to radiation emitted from the target region, and is substantially not responsive to radiation emitted from outside the target region.

In the present invention, the signal (scattering, reflection and/or fluorescence) originating from the target region is separated from the signal (scattering, reflection and/or fluorescence) originating from outside the target region by electrical spectral filtering, as opposed to optical spatial filtering as in prior confocal microscopes. As a result, the requirements on the optical design of the collection assembly can be greatly reduced, which can provide reduced cost and/or improved performance.

BRIEF DESCRIPTION OF THE DRAWINGS

FIGS. 5a and 5b show a collection assembly according to an embodiment of the invention.

FIGS. 6a and 6b show operation of the collection assembly of FIGS. 5a and 5b.

DETAILED DESCRIPTION

Figure 1:
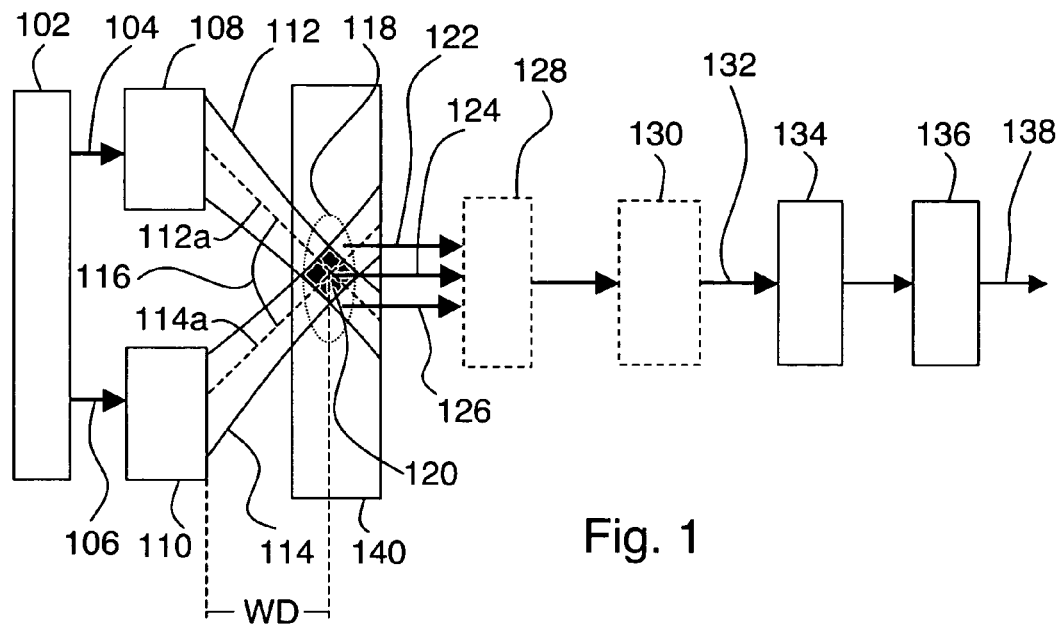
FIG. 1 shows a confocal microscope according to an embodiment of the invention.

FIG. 1 shows a confocal microscope according to an embodiment of the invention. An optical source assembly 102 provides a first optical beam 104 and a second optical beam 106. Optical beams 104 and 106 differ in frequency by a coherent frequency difference $\Delta f$ (i.e., beams 104 and 106 are mutually coherent). Optical beams 104 and 106 are preferably laser beams. Typically a beamsplitter is employed to provide two laser beams from a single source. The single laser source is preferably a continuous wave (CW) laser diode having a wavelength selected to efficiently excite fluorescence from a sample of interest. In biological applications, penetration depth increases with wavelength, but resolution decreases as wavelength increases, resulting in a trade between resolution and penetration depth. A preferred laser wavelength range for biological applications is from about 400 nm to about 1,500 nm.

Figure 2:
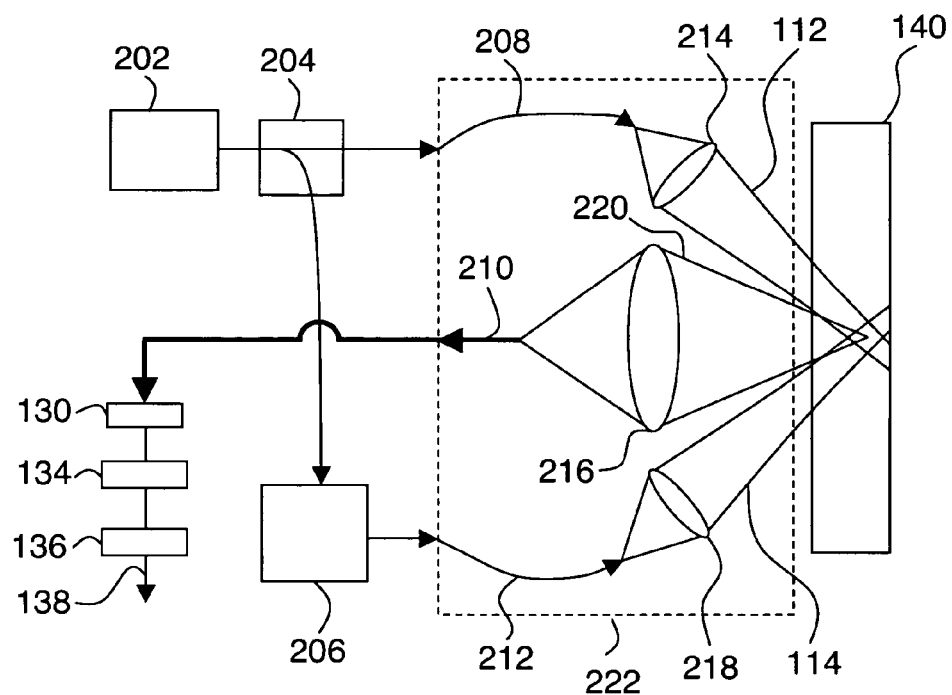
FIG. 2 shows a confocal microscope according to another embodiment of the invention.

Mutually coherent beams having a coherent frequency difference $\Delta f$ can be provided in various ways, such as frequency offset locking a slave laser to a master laser with a phase locked loop, injection locking a slave laser to a modulation sideband of a master laser, or, preferably, using an acousto-optic (AO) frequency shifter (as shown on FIG. 2). Mutual coherence of beams 104 and 106 (or, equivalently, a coherent frequency difference $\Delta f$) is present if superposition of beams 104 and 106 gives rise to intensity modulation at a frequency $\Delta f$ due to interference.

First optical beam 104 is received by a first focusing assembly 108, which provides a first focused beam 112 to a sample 140. Similarly, second optical beam 106 is received by a second focusing assembly 110, which provides a second focused beam 114 to sample 140. First and second focused beams 112 and 114 intersect in a target region 120 (shaded) of sample 140. Target region 120 preferably lies within the focal regions of focused beams 112 and 114. Here the focal region of a beam focused by a lens in a medium is defined to be the range $|z|<z_r$, where z is distance along the beam axis, $z=0$ at the focal plane of the beam, and $z_r=\lambda/nNA_0^2$ where $\lambda$ is the free space wavelength, n is the refractive index of the medium, and $NA_0=\sin\theta$ where $\theta$ is the angle between the lens axis and a line extending from the lens focal point to the edge of the lens aperture. First and second focusing assemblies 108 and 110 are shown as blocks on FIG. 1 because any arrangement of optical elements that provides focused beams 112 and 114 given optical beams 104 and 106 is suitable for practicing the invention. Focusing assemblies 108 and 110 can include lenses, curved mirrors, planar mirrors, diffractive optical elements or any combination thereof. Preferably, first and second focusing assemblies 108 and 110 are appropriately positioned low NA lenses (i.e., NA<0.3) to reduce cost, and to provide a long working distance.

Focused beams 112 and 114 have beam axes 112a and 114a respectively, and have a beam intersection angle 116. Beam intersection angle 116 is preferably between about 45 degrees and about 90 degrees, and is more preferably about 60 degrees, in order to minimize the size of target region 120 while providing a suitable working distance (i.e., the distance WD between focusing assembly 108 (or 110) and target region 120 on FIG. 1). In some cases, aberration incurred when focused beams 112 and 114 enter sample 140 at an oblique angle are negligible. In other cases, where these aberrations are not negligible, a prism or prisms can be used in front of sample 140 to reduce or eliminate coma and/or astigmatism.

Light emitted from a collection region 118 within sample 140 is ultimately received as detector input light 132 by detector 134. Between sample 140 and detector 134 an optional collection assembly 128 and/or an optional optical filter 130 may be present. The dimensions of collection region 118 are defined by collection assembly 128 (if present), or by the aperture of detector 134 (if collection assembly 128 is absent). Collection region 118 includes part or all of target region 120, and may also include parts of sample 140 outside of target region 120. Thus the light emitted from collection region 118 includes light 124 emitted from target region 120, and may also include light (122 and 126) emitted from outside of target region 120.

Furthermore, light collected from collection region 118 can also include multiply scattered light. For example, light emitted from a point in sample 140 can be scattered from one or more additional points in sample 140 before being collected. Such light is referred to as multiply scattered light. Since multiple scattering is possible, it is helpful to distinguish between light originating from a point P in sample 140 and light emitted from a point P in sample 140. Light emitted from P includes all light radiated away from P. Light originating from P is all light radiated away from P that is responsive to an external input at P (i.e., excluding only light generated elsewhere in sample 140 and scattered from P). Reflection, linear scattering, and linear and nonlinear fluorescence are all included in light originating from P.

Radiation 124 from target region 120 is modulated with modulation frequency $\Delta f$. The reason for this is that in target region 120, mutually coherent focused beams 112 and 114 are superposed, and therefore interfere. Let $U_1$ and $U_2$ (both being vector functions of x, y, and z) be the position-dependent electric field amplitudes of beams 112 and 114 respectively in target region 120. The corresponding time dependent amplitudes are $U_1$ and $U_2 \exp(\pm i2\pi\Delta f t)$, where both alternatives for the sign of $\Delta f$ are explicitly accounted for by the $\pm$ sign. The time-dependent optical intensity $I(t)=|U_1+U_2 \exp(\pm i2\pi\Delta ft)|^2=|U_1|^2+|U_2|^2+2|U_1 \cdot U_2|\cos(2\pi\Delta ft)$. Thus the incident optical intensity in target region 120 is modulated with frequency $\Delta f$. Note that the sign of $\Delta f$ has no effect on I(t). All of the physical processes which can provide output radiation from target region 120 responsive to input radiation provide an output which depends on input intensity. For this reason, radiation 124 is modulated with frequency $\Delta f$.

Preferably, $|U_1|$ is roughly equal to $|U_2|$ within target region 120, so that the modulation depth of I(t) is at or near its maximum value. Also, the modulated term in I(t) depends on the dot product $U_1 \cdot U_2$, which is maximal if beams 112 and 114 have the same polarization, and is zero if beams 112 and 114 are orthogonally polarized. Accordingly, it is preferred for beams 112 and 114 to have the same polarization, or substantially the same polarization within target region 120, so that the modulated term in I(t) is at or near its maximum value. In the example of FIG. 1, if beams 112 and 114 are both polarized out of the plane of the figure, they will have the same polarization in target region 120.

If present, collection assembly 128 collects radiation from collection region 118 and provides the collected radiation as detector input radiation 132 to detector 134. Collection assembly 128 is shown as a block on FIG. 1 because any arrangement of optical elements that provides detector input radiation 132 given optical radiation from collection region 118 is suitable for practicing the invention. Collection assembly 128 can include a lens, a curved mirror, a planar mirror, a multimode optical fiber, a light pipe, a diffractive optical element, or any combination thereof. Preferably, collection assembly 128 is an appropriately positioned high NA lens (i.e., NA>0.5) to collect as much light from target region 120 as possible. Light from target region 120 is typically emitted in all directions, so increasing the NA of collection assembly 118 increases the amount of light collected.

If present, optical filter 130 spectrally filters radiation emitted from collection region 118 and provides filtered radiation as detector input radiation 132 to detector 134. Various physical processes can contribute to light emitted from sample 140, such as linear scattering and/or reflection (at $\lambda_p$, where $\lambda_p$ is the wavelength of beams 112 and 114), one-photon fluorescence (typically at $\lambda > \lambda_p$), two-photon fluorescence (typically at $\lambda > \lambda_p/2$), and second harmonic generation (at $\lambda = \lambda_p/2$). Typically, the linear scattering and/or reflection signal is the strongest of these signals, and so in cases where another signal is of interest, it is preferred to filter out radiation at $\lambda_p$. More preferably, optical filter 130 is a bandpass optical filter passing the signal of interest and blocking as much other light emitted from sample 140 as possible. Optical filter 130 can be a thin-film interference filter, a colored glass filter, a holographic notch filter, a prism or grating-based filter, etc.

In some cases it may be desirable to perform simultaneous reflection and fluorescence microscopy. For this purpose a beamsplitter can be used to split light collected from collection region 118 into two paths, each path having a bandpass optical filter centered on the respective wavelength of interest. Separate photodetectors can be used in the two paths to provide independent reflection and fluorescence signals.

Detector input radiation 132 is received by detector 134. As indicated above, detector input radiation 132 is emitted from sample 140, and may pass through collection assembly 128 and/or through optical filter 130 before reaching detector 134. Detector input radiation 132 includes radiation 124 emitted from target region 120 and may include radiation, such as 122 and 126, emitted from outside target region 120. Detector 134 must have a bandwidth that includes $\Delta f$, so that an electrical signal provided by detector 134 is modulated responsive to modulation of detector input radiation 132 at $\Delta f$. Detector 134 can be a semiconductor photodiode (e.g., a Si or InGaAs photodiode), a photomultiplier tube, or any other device that provides an electrical signal responsive to received optical intensity.

Figure 9:
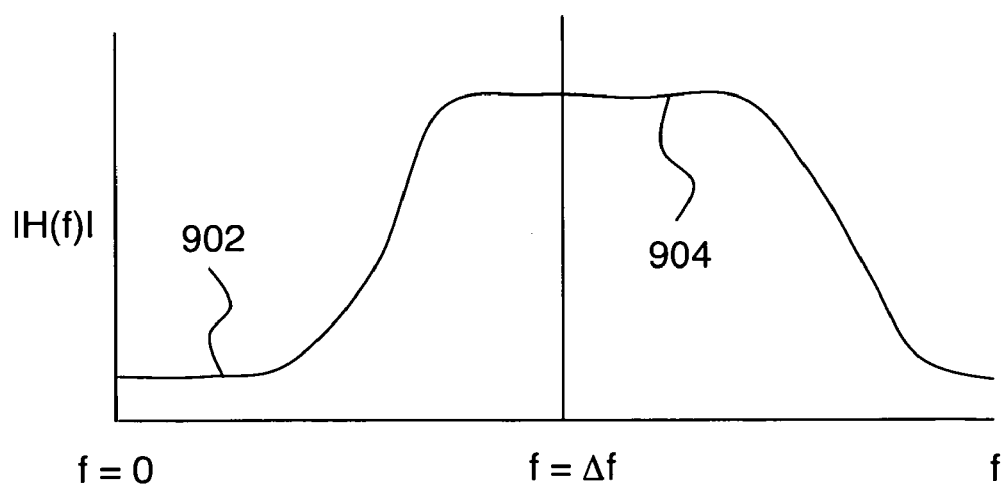
FIG. 9 shows electrical filtering in accordance with an embodiment of the invention.

The electrical signal provided by detector 134 is received by an electrical filter 136, which provides a filtered electrical signal 138. An exemplary frequency response H(f) for filter 136 is shown on FIG. 9, which has a pass band 904 including $f=\Delta f$, and has a stop band 902 including $f=0$. Thus filtered signal 138 provided by filter 136 is responsive to radiation originating from target region 120 (which is modulated at $\Delta f$ and thus is passed by pass band 904). Filtered signal 138 is substantially not responsive to non-modulated radiation originating from outside target region 120 (which is not modulated and thus is blocked by stop band 902). Filter 136 can be any electrical filter that provides a pass band including $f=\Delta f$ and a stop band including $f=0$, including but not limited to: a passive analog filter, a digital filter, and a filter provided by lock-in detection.

Thus filter signal 138 is a suitable output signal for a confocal microscope, since it is selectively responsive to light originating from target region 120, even if collection region 118 includes illuminated parts of sample 140 outside of target region 120. In other words, according to the invention, light originating from target region 120 is separated from light originating from outside of target region 120 by spectral electrical filtering, as opposed to the optical spatial filtering of the prior art. As a result, the requirements on the optical design of collection assembly 128 can be greatly reduced, which can provide reduced cost and/or improved performance. In particular, chromatic and non-chromatic aberration in collection assembly 128 has little or no impact on microscope performance. Furthermore, the lenses on the input beams are only required to operate at the emission wavelength of optical source assembly 102. This simplifies their design, and makes it possible to use dispersive lenses such as Fresnel lenses or simple single aspheric or graded-index (GRIN) lenses despite the typically high chromatic aberration of such lenses.

For example, we can compare the signal provided by the embodiment of FIG. 1 to the signal provided by a prior art dual axis confocal microscope using one beam for illumination and the other beam for receiving. Let the total optical power emitted from the target region of the prior art microscope be $P_0$. Isotropic emission into a $4\pi$ solid angle is assumed. The collected optical power is $P_c=P_0(1-\cos\theta)/2$, where $\sin\theta$ is the free-space numerical aperture ($NA_0$) of the collecting lens and $\theta$ is the half-angle of the collected cone of light. Typically, prior art dual illumination beam confocal microscopes have relatively low lens $NA_0$ to reduce aberration. In this example, we assume a lens $NA_0$ of 0.15, which gives $P_c=5.6e-3\ P_0$.

To compare this example with an example according to an embodiment of the invention, let $P_1$ be the modulated power emitted from the target region. We assume the two illumination beams have equal power and the same polarization, so that $P_1=P_0/2$ and thus $P_c=P_0(1-\cos\theta)/4$. Here we assume a lens $NA_0$ of 0.8, which gives $P_c=0.1\ P_0$. Comparing the two signals shows that the use of a large NA lens according to an embodiment of the invention provides a signal that is nearly 18 times larger than the signal provided by the low NA prior art microscope. It is important to note that it would not be straightforward to increase the lens NA in the prior art microscope to such a large value as 0.8, because the prior art microscope relies on low lens aberration which is difficult to obtain in high NA lenses.

FIG. 2 shows a confocal microscope according to another embodiment of the invention. In the embodiment of FIG. 2, a laser 202 is fiber coupled to a fiber optic splitter 204, which splits the input laser power evenly or unevenly between its two outputs. Preferably, splitter 204 splits the optical power from laser 202 such that beams 112 and 114 incident on sample 140 have equal or approximately equal power. One output of splitter 204 is fiber coupled to an acousto-optic (AO) frequency shifter 206. AO frequency shifter 206 provides an output optical signal that is frequency shifted relative to its input by a frequency shift $\Delta f$. Typically, the frequency shift $\Delta f$ is selected by applying an electrical signal (not shown) having frequency $\Delta f$ to AO frequency shifter 206. The frequency shift $\Delta f$ between output and input of AO frequency shifter 206 can be either positive or negative, and as indicated above, the sign of $\Delta f$ is irrelevant to the operation of the invention. Typical values for $\Delta f$ provided by AO frequency shifter 206 are in a range from about 10 MHz to about 150 MHz (e.g., $\Delta f$=80 MHz is used in some of our experiments).

Splitter 204 is connected to a first optical fiber 208, which emits radiation that is received by a first focusing lens 214 to provide first focused beam 112 illuminating sample 140. Thus the arrangement of fiber 208 and lens 214 acts as first focusing assembly 108 of FIG. 1. Similarly, AO frequency shifter 206 is connected to a second optical fiber 212, which emits radiation that is received by a second focusing lens 218 to provide second focused beam 114 to sample 140. Thus the arrangement of fiber 212 and lens 218 acts as second focusing assembly 110 of FIG. 1. Laser 202, splitter 204, AO frequency shifter 206 and fibers 208 and 212 together act as an optical source assembly 102 of FIG. 1. Radiation 220 is emitted from sample 140, and is collected by a collection lens 216, which couples radiation 220 to a multi-mode optical fiber 210. Thus the arrangement of fiber 210 and lens 216 acts as collection assembly 128 of FIG. 1. The remaining elements on FIG. 2 (i.e., optical filter 130, detector 134, electrical filter 136 and filtered signal 138) are as discussed above in connection with FIG. 1. All of the optical fibers shown on FIG. 2, with the exception of multi-mode fiber 210, are single-mode fibers.

The optical path lengths taken by beams 112 and 114 to arrive at sample 140 from laser 202 are preferably approximately equal and more preferably equal, since equality of path lengths maximizes the strength of the interference between beams 112 and 114 in sample 140. Radiation emitted by laser 202 has a characteristic length, often referred to as the coherence length Lc. Path length differences much less than Lc have a negligible effect on interference, and path length differences much greater than Lc essentially eliminate interference entirely. Thus there is no need to achieve exact path length matching in practice, since it suffices to match the path lengths to a precision of about Lc. Typical CW laser sources have Lc on the order of 10 cm or more.

Figure 3:
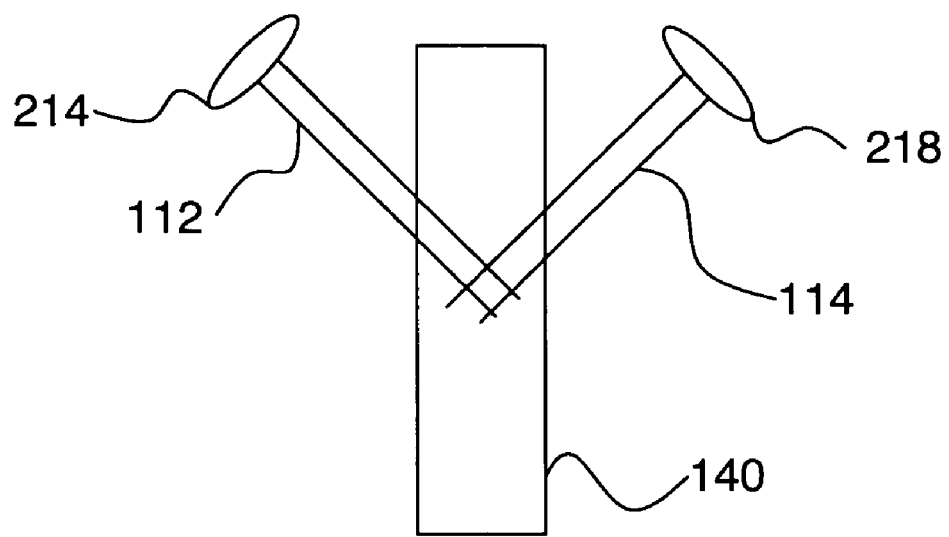
FIG. 3 shows an arrangement of focusing assemblies according to an embodiment of the invention.
Figure 4:
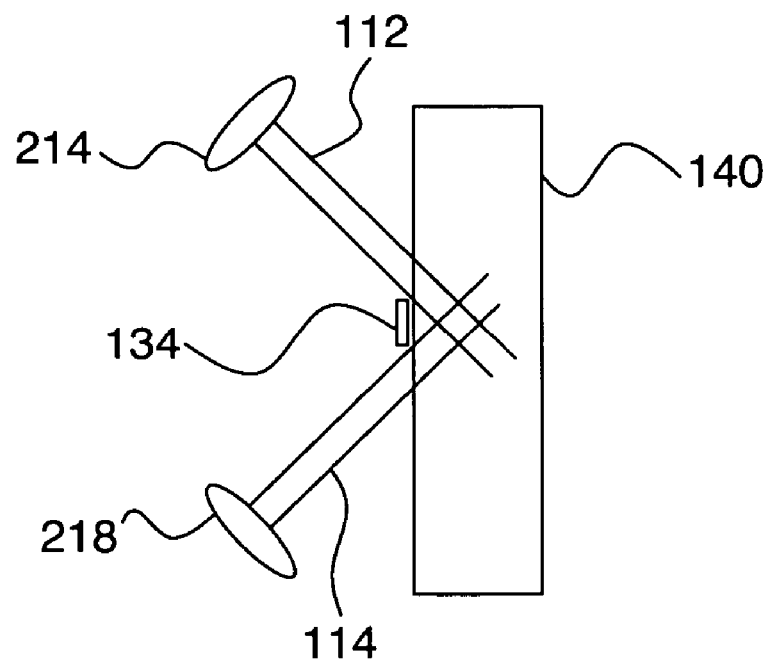
FIG. 4 shows an arrangement of a detector according to an embodiment of the invention.

In the embodiment of FIG. 2, beams 112 and 114 are on the same side of sample 140 as the collection assembly (i.e., lens 216 and fiber 210). On FIG. 1, collection assembly 128 is on the opposite side of sample 140 from beams 112 and 114, which is most appropriate if sample 140 is transparent and/or thin. Other suitable optical arrangements for practicing the invention are shown on FIGS. 3 and 4. FIG. 3 shows two illumination beams coming from opposite sides of the sample. FIG. 4 shows a detector placed in close proximity to the sample. In the example of FIG. 4, a separate collection assembly, such as 128 on FIG. 1, is not present. Generally, any optical arrangement that provides intersecting illumination beams and collection of radiation emitted from the region where the illumination beams intersect is suitable for practicing the invention.

The embodiment of FIG. 2 is fiber coupled, which allows a microscope head 222 to be disposed in proximity to sample 140 and remotely from the other components making up the microscope, such as laser 202, AO frequency shifter 206, optical filter 130, detector 134 and electrical filter 136. Such separation of microscope head 222 from the other elements of the microscope is advantageous, in that microscope head 222 can be miniaturized and/or adapted for various applications without having to locally include the other elements of the microscope. In order to ensure that beams 112 and 114 have the same state of polarization at sample 140, it is preferable for polarization maintaining (PM) fiber to be used for all optical fibers shown on FIG. 2 (except multi-mode fiber 210). In this manner, the polarization of beams 112 and 114 at sample 140 can be set appropriately (i.e., to be perpendicular to the plane of FIG. 2) by appropriately orienting the end faces of fibers 208 and 212.

Naturally, other methods of setting the polarizations of beams 112 and 114 can also be used to practice the invention. For example, polarization controllers in a standard single mode fiber arrangement (instead of PM fiber) could be used to set the states of polarization of beams 112 and 114 to be the same. Another example is the use of Lyot depolarizers, since depolarized beams cannot be orthogonally polarized and will therefore always provide a modulated signal.

In cases where illumination and collection are performed on the same side of sample 140, the collection optics (e.g., lens 216 on FIG. 2) must not block focused beams 112 and 114. This requirement for non-blocking can limit the amount of light collected from target region 120. However, there are various ways to increase light collection while accommodating the illumination beams. For example, the arrangement of FIG. 4 shows a detector placed in close proximity to sample 140, which can collect light from nearly the full angle subtended by beams 112 and 114. The arrangement of FIG. 4 is preferably implemented as a miniaturized fiber-coupled confocal microscope head (such as 222 on FIG. 2 with an electrical output instead of fiber output 210). Such a microscope head can be fabricated with MEMS technology.

Another light collection arrangement is shown on FIGS. 5a and 5b. On FIG. 5a, a transparent light pipe 502 collects radiation 504 from sample 140 and transmits it to detector 134. Notches, as shown in the end view of FIG. 5b, are present in light pipe 502 to accommodate beams 112 and 114. In this manner, light can be collected from a solid angle larger than the solid angle subtended by beams 112 and 114. On FIGS. 5a and 5b, light pipe 502 is shown with a circular cross section. Other cross sections are also suitable for practicing the invention. For example, light pipe 502 could have a rectangular cross section, where the long dimension of the rectangle is perpendicular to the plane of FIG. 5a (and thus does not interfere with beams 112 and 114), while the short dimension of the rectangle fits in between beams 112 and 114.

FIG. 6a shows the operation of light pipe 502 on FIGS. 5a and 5b. On FIG. 6a, light is incident on an end face 606 of a light pipe 602 with an angle of incidence $\alpha$, and is transmitted with an angle of transmission $\beta$. The transmitted light is then incident on a side wall of light pipe 602 with angle of incidence γ. Note that each subsequent angle of incidence after the first is equal to the first angle of incidence, so it is only necessary to consider the first reflection. Let m be the ratio of the refractive index of light pipe 602 to the refractive index of the medium surrounding the light pipe. Light will be trapped in light pipe 602 if it is totally reflected at the side walls, which will be the case if sin γ>1/m. From the geometry of FIG. 6a, sin γ=cos β, so we have cos β>1/m as the condition for light trapping. Snell's law at end face 606 gives m sin β=sin α. Combining these relations gives $\sin^2 \alpha < m^2 - 1$ as the condition for light trapping. Thus if $m^2 > 2$ (i.e., m>1.414), all of the light incident on end face 606 will be trapped within light pipe 602 and transmitted to detector 134, since all possible angles of incidence α will satisfy the trapping condition. Such a light pipe completely traps light incident on its end face 606.

If light pipe 602 is surrounded by air, the complete trapping condition is satisfied if light pipe 602 is made of a material having an index $n_{pipe} > 1.414$. Many varieties of glass have a sufficiently high index to meet this condition (e.g., silica having n=1.46). If light pipe 602 is surrounded by a material such as water or biological tissue (typical n=1.35), then a higher index is required for light pipe 602 to satisfy the complete trapping condition ($n_{pipe}=1.909$ in this example).

FIG. 6b shows the use of a tapered light pipe 604 to collect light. Tapered light pipe 604 can satisfy the complete trapping condition using a lower index of refraction than an un-tapered light pipe 602. The reason for this is that the angle of incidence γ on FIG. 6b is equal to π/2−β+δ (compared to γ=π/2−β on FIG. 6a), which makes the complete trapping condition easier to achieve. Note that each subsequent angle of incidence after the first is larger than the first angle of incidence, so it is only necessary to consider the first reflection. More specifically, the complete trapping condition in this case is given by $m^2 > 2/(1+\sin \delta)$. For example, if δ=10 degrees, we have m>1.305 for complete trapping.

Figure 7A:
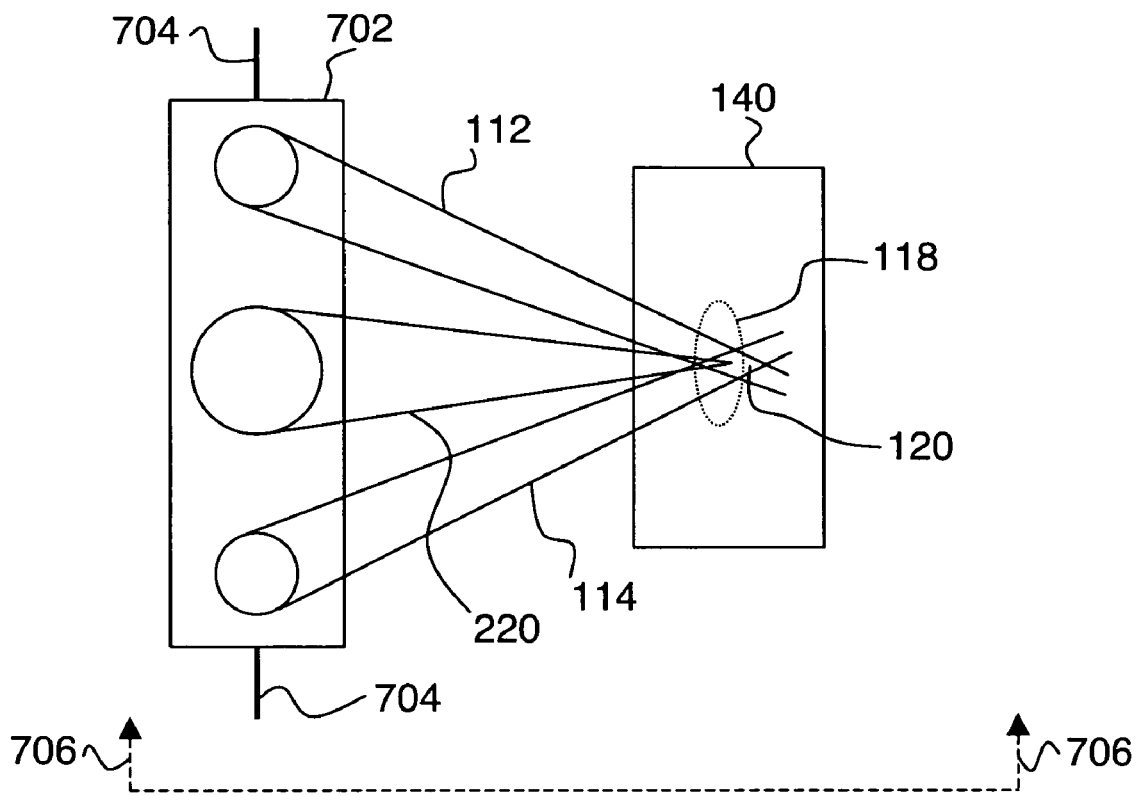
FIGS. 7a and 7b show a scanning assembly according to an embodiment of the invention.
Figure 7B:
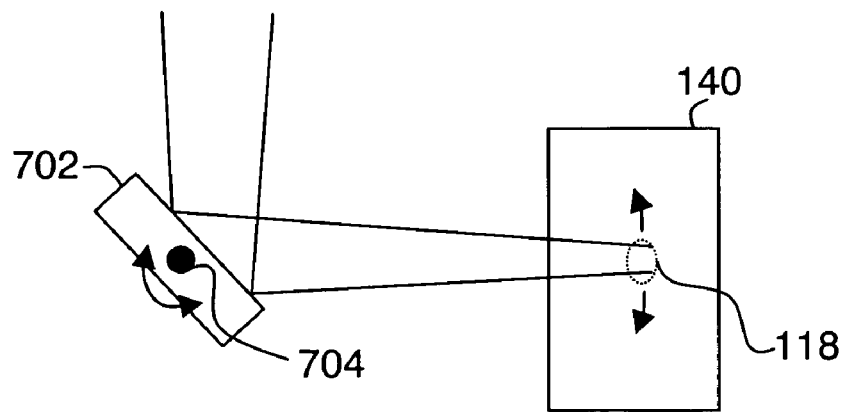

FIGS. 7a and 7b show a scanning assembly according to an embodiment of the invention. On FIG. 7a, beams 112 and 114 are incident from above the plane of FIG. 7a on a scanning mirror 702 and are reflected by scanning mirror 702 to sample 140. Radiation 220 emitted from sample 140 is also incident on and reflected by scanning mirror 702. Scanning mirror 702 is rotatably mounted about a rotation axis 704. An end view of the arrangement of FIG. 7a in the direction indicated by 706 on FIG. 7a is shown on FIG. 7b. FIG. 7b shows that rotation of mirror 702 about axis 704 will scan collection region 118 within sample 140 as shown. Furthermore, target region 120 defined by the intersection of beams 112 and 114 is also scanned within sample 140 by rotation of mirror 702. An advantage of this scanning arrangement is that a single scanning element (i.e., mirror 702) scans the target and collection regions together within sample 140.

In the arrangement of FIGS. 7a and 7b, it is preferable for beams 112 and 114 to be p-polarized with respect to scanning mirror 702, since this arrangement of polarizations at mirror 702 ensures that beams 112 and 114 have nearly the same polarization at sample 140. Conversely, if beams 112 and 114 are s-polarized at mirror 702, they will not have the same polarization in sample 140, so this polarization configuration is not preferred.

Figure 8:
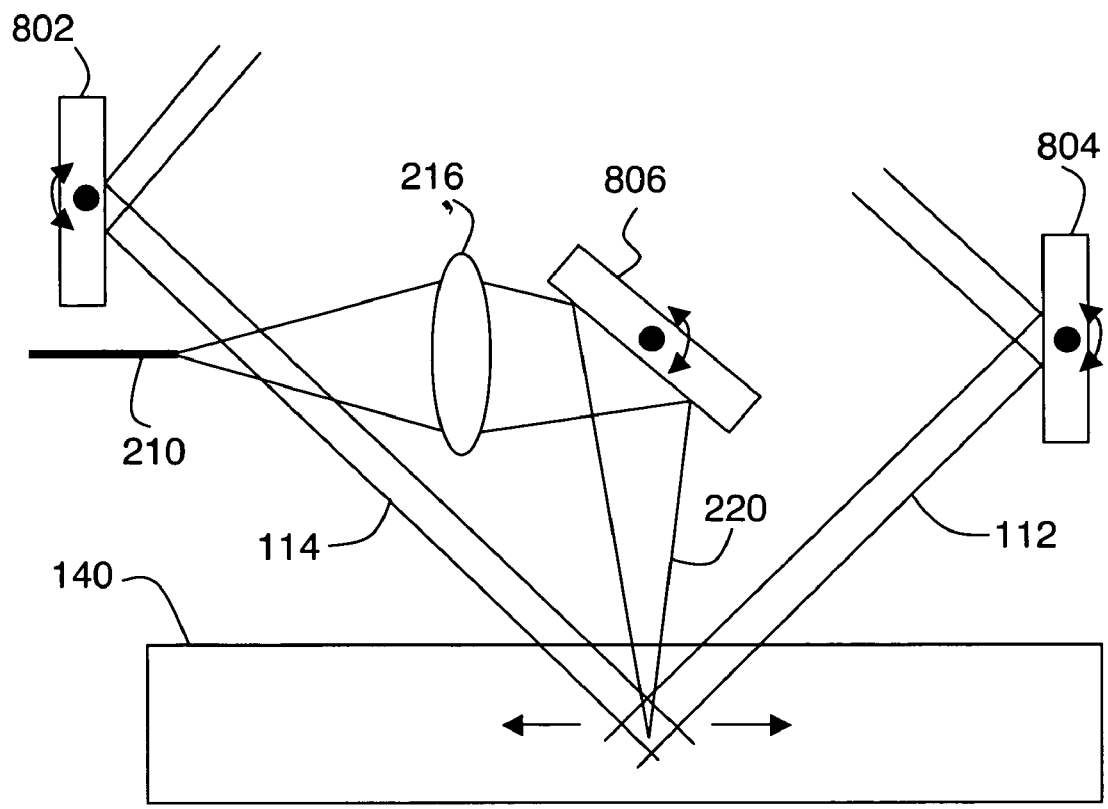
FIG. 8 shows an alternate scanning assembly according to an embodiment of the invention.

FIG. 8 shows an alternate scanning assembly according to an embodiment of the invention. On FIG. 8, beam 112 is reflected from a first scanning mirror 804 to sample 140, and beam 114 is reflected from a second scanning mirror 802 to sample 140. Radiation 220 emitted from sample 140 is incident on a third scanning mirror 806 and is collected by lens 216 which couples radiation 220 to multimode fiber 210. Scanning mirrors 802, 804, and 806 can all rotate about the indicated axes. Thus, by rotating mirrors 802, and 804 in a coordinated manner, the target region formed by the intersection of beams 112 and 114 can be scanned within sample 140 as indicated. Furthermore, mirror 806 can be rotated in coordination with mirrors 802 and 804 to provide collection of radiation 220 from the target region. Alternatively, the field of view of the collection assembly may be sufficiently large that there is no need to scan collection region 118 along with the target region.

In the arrangement of FIG. 8, it is preferable for beams 112 and 114 to be s-polarized at mirrors 804 and 802 respectively, since this arrangement of polarizations at mirrors 804 and 802 ensures that beams 112 and 114 have the same polarization at sample 140. Conversely, if beams 112 and 114 are p-polarized at mirror 804 and 802 respectively, they will not have the same polarization in sample 140, so this polarization configuration is not preferred.

The scanning arrangements of FIGS. 7a and 7b, and of FIG. 8 can be combined to provide 2-D scanning within sample 140. In such a combination, the preferred polarization conditions on mirror 702 and on mirrors 802 and 804 can be achieved simultaneously, to provide beams 112 and 114 having the same, or nearly the same, state of polarization in sample 140.

The preceding detailed description has been exemplary, and accordingly many modifications of the above embodiments are also suitable for practicing the invention. For example, collection and illumination beams need not be coplanar with the target region as shown in the above embodiments. An alternative arrangement is roughly tetrahedral, where the four vertices of the tetrahedron are target region 120, first focusing assembly 108, second focusing assembly 110 and collection assembly 128. Such an arrangement reduces interference between collection assembly 128 and beams 112 and 114 by tilting collection assembly 128 away from a plane containing beams 112 and 114.

Another alternative embodiment is the use of a pulsed laser source as opposed to the CW sources used in the above preferred embodiments. Short pulse excitation (e.g., pulse duration on the order of 100 fs or less) is advantageous for microscopy based on nonlinear fluorescence (e.g., two-photon fluorescence), since the high intensity provided by such pulses preferentially increases nonlinear signals compared to linear signals. A preferred method of establishing a coherent frequency difference Δf between two pulsed laser beams is to employ the arrangement of FIG. 2 using a splitter and an AO frequency shifter to provide the coherent frequency difference Δf. The pulses arriving at target region 120 must overlap in time in order for interference to occur.

The effect of interference depends on the pulse duration τ and frequency difference Δf. If τ>>1/Δf, then interference between the two beams manifests as optical intensity variation within a pulse. If τ<<1/Δf, interference between the two beams manifests as optical intensity variation from pulse to pulse (i.e., the pulse train has an envelope modulated at Δf). A detector having a time constant Td such that τ<<Td<<1/Δf is suitable for detecting such envelope modulation.

As indicated in connection with FIG. 2, path length matching from source to target of the two interfering beams to within about Lc or less is required in order to obtain interference. For pulsed laser sources, the coherence length Lc can be rather small (e.g., on the order to about 10 to about 20 microns). Thus, the required precision of path length matching for the pulsed laser embodiment is significantly greater than for typical CW laser embodiments.

What is claimed is:

1. A dual-beam confocal microscope comprising:
a) an optical source assembly providing first and second optical beams having a nonzero coherent frequency difference Δf between said first and second beams;
b) a first focusing assembly receiving said first optical beam and providing a first focused beam having a first focal region and illuminating a sample;
c) a second focusing assembly receiving said second optical beam and providing a second focused beam having a second focal region and illuminating said sample, wherein said first and second focused beams intersect within a target region in said sample at a beam intersection angle;
d) a detector receiving detector input radiation emitted from said sample and providing an electrical signal responsive to an intensity of said detector input radiation, wherein said detector input radiation includes radiation emitted from said target region;
e) an electrical filter receiving said electrical signal and providing a filtered electrical signal, wherein said filter has a frequency response H(f) having a pass band including f=Δf and a stop band including f=0; and
f) a target region scanner for moving at least one of said first and second focused beams such that said target region is scanned within said sample;
whereby said filtered signal is responsive to radiation originating from said target region and is substantially not responsive to radiation originating from outside said target region.

2. The microscope of claim 1, wherein said first and second focused beams are pulsed beams.

3. The microscope of claim 1, wherein said first and second focused beams are continuous-wave beams.

4. The microscope of claim 1, wherein said target region overlaps with said first and second focal regions.

5. The microscope of claim 1, wherein said first and second focused beams have substantially the same state of polarization within said target region.

6. The microscope of claim 1, wherein said optical source assembly comprises a laser and an acousto-optic (AO) frequency shifter providing said frequency difference Δf.

7. The microscope of claim 6, wherein said first beam has a first path length between said laser and said target region and said second beam has a second path length between said laser and said target region, and wherein said first and second path lengths differ by less than a coherence length of said laser light.

8. The microscope of claim 1, wherein said optical source assembly further comprises first and second single-mode optical fibers from which said first and second beams, respectively, are emitted.

9. The microscope of claim 1, wherein said first focusing assembly comprises a member selected from the group consisting of: a lens, a curved mirror, a planar mirror, a diffractive optical element, and combinations thereof.

10. The microscope of claim 9, wherein said first focusing assembly comprises a lens having NA<0.3.

11. The microscope of claim 1, wherein said second focusing assembly comprises a member selected from the group consisting of: a lens, a curved mirror, a planar mirror, a diffractive optical element, and combinations thereof.

12. The microscope of claim 11, wherein said second focusing assembly comprises a lens having NA<0.3.

13. The microscope of claim 1, wherein said beam intersection angle is between about 45 degrees and about 90 degrees.

14. The microscope of claim 13, wherein said beam intersection angle is about 60 degrees.

15. The microscope of claim 1, wherein said first and second focusing assemblies are disposed on opposite sides of said sample.

16. The microscope of claim 1, wherein said first and second focusing assemblies are disposed on a first side of said sample.

17. The microscope of claim 1, further comprising: an optical filter receiving radiation emitted from said sample and providing filtered radiation as said detector input radiation.

18. The microscope of claim 17, wherein said optical filter passes single-photon fluorescence from said target region and blocks linear scattering from said target region.

19. The microscope of claim 17, wherein said optical filter passes two-photon fluorescence from said target region and blocks linear scattering from said target region.

20. The microscope of claim 17, wherein said optical filter passes second-harmonic radiation from said target region and blocks linear scattering from said target region.

21. The microscope of claim 1, further comprising: a collection assembly collecting optical radiation emitted from a collection region of said sample that includes part or all of said target region, and providing said collected radiation as said detector input radiation.

22. The microscope of claim 21, wherein said collection assembly comprises a member selected from the group consisting of: a lens, a curved mirror, a planar mirror, a multimode fiber, a light pipe, a diffractive optical element, and combinations thereof.

23. The microscope of claim 22, wherein said collection assembly comprises a lens having NA>0.5.

24. The microscope of claim 21, wherein said first and second focusing assemblies are disposed on a first side of said sample and wherein said collection assembly is disposed on a second side of said sample opposite to said first side.

25. The microscope of claim 21, wherein said first and second focusing assemblies are disposed on a first side of said sample and wherein said collection assembly is disposed on said first side of said sample.

26. The microscope of claim 25, wherein said collection assembly comprises a cylindrical light pipe having an end face in proximity to said target region.

27. The microscope of claim 26, wherein said light pipe has notches in its cylindrical surface and extending to said end face, and wherein said first and second beams are in said notches.

28. The microscope of claim 21, further comprising:
a collection region scanner for moving said collection region together with said target region within said sample.

29. A method for performing dual-beam confocal microscopy, the method comprising:
a) illuminating a sample with a first focused optical beam having a first focal region;
b) illuminating said sample with a second focused optical beam having a second focal region, wherein said first and second focused beams intersect within a target region in said sample at a beam intersection angle;

c) establishing a nonzero coherent frequency difference $\Delta f$ between said first and second optical beams;
d) collecting optical radiation emitted from a collection region of said sample that includes part or all of said target region;
e) detecting an intensity of part or all of said collected optical radiation to provide an electrical signal;
f) filtering said electrical signal with an electrical filter to provide a filtered signal, said filter having a frequency response H(f) having a pass band including $f=\Delta f$ and a stop band including $f=0$; and
g) moving at least one of said first and second focused beams such that said target region is scanned within said sample whereby said filtered signal is responsive to radiation originating from said target region and is substantially not responsive to radiation originating from outside said target region.

30. The method of claim 29, wherein said first and second focused beams are pulsed beams.

31. The method of claim 29, wherein said first and second focused beams are continuous-wave beams.

32. The method of claim 29, wherein said target region overlaps with said first and second focal regions.

33. The method of claim 29, wherein said first and second focused beams have substantially the same state of polarization within said target region.

34. The method of claim 29, wherein said establishing a frequency difference $\Delta f$ comprises passing light from a laser through an acousto-optic (AO) frequency shifter.

35. The method of claim 34, wherein said first focused beam has a first path length between said laser and said target region and said second focused beam has a second path length between said laser and said target region, and further comprising providing said first and second path lengths which differ by less than a coherence length of said laser light.

36. The method of claim 29, further comprising filtering said collected radiation with an optical filter to provide a filtered part of said collected radiation.

37. The method of claim 36, wherein said optical filter passes single-photon fluorescence from said target region and blocks linear scattering from said target region.

38. The method of claim 36, wherein said optical filter passes two-photon fluorescence from said target region and blocks linear scattering from said target region.

39. The method of claim 36, wherein said optical filter passes second-harmonic radiation from said target region and blocks linear scattering from said target region.

40. The method of claim 29, further comprising:
moving said collection region together with said target region within said sample.

* * * * *

UNITED STATES PATENT AND TRADEMARK OFFICE
CERTIFICATE OF CORRECTION

PATENT NO.         : 7,130,042 B2                                            Page 1 of 1
APPLICATION NO.    : 10/794561
DATED              : October 31, 2006
INVENTOR(S)        : Gordon S. Kino It is certified that error appears in the above-identified patent and that said Letters Patent is hereby corrected as shown below:

Title Page, Item (75)

Inventors: Gordon S. Kino, Stanford, CA (US)
           Michael J. Mandella, Cupertino, CA (US)

should be

Inventors: Gordon S. Kino, Stanford, CA (US)
           Michael J. Mandella, Cupertino, CA (US)
           Thomas D. Wang, Mountain View, CA (US)

Signed and Sealed this

Twenty-seventh Day of March, 2007

JON W. DUDAS
*Director of the United States Patent and Trademark Office*